United States Patent [19]

Atherton et al.

[11] 4,234,478

[45] Nov. 18, 1980

[54] PROCESS AND APPARATUS FOR THE DIAZOTIZATION OF AMINES

[75] Inventors: John H. Atherton; Ian Hodgkinson, both of Manchester, England

[73] Assignee: Imperial Chemical Industries Limited, London, England

[21] Appl. No.: 10,478

[22] Filed: Feb. 8, 1979

[30] Foreign Application Priority Data

Feb. 14, 1978 [GB] United Kingdom ............... 581978/78
Nov. 20, 1978 [GB] United Kingdom ............... 45292/78

[51] Int. Cl.³ ............................................ C07C 113/00
[52] U.S. Cl. ............................... 260/141; 422/111
[58] Field of Search ................................. 260/141 P

[56] References Cited

U.S. PATENT DOCUMENTS

| 1,585,145 | 5/1926 | Harris | 260/141 P |
| 3,117,954 | 1/1964 | Hupfer | 260/141 P |
| 3,423,391 | 1/1969 | Kindler | 260/141 P |

FOREIGN PATENT DOCUMENTS

| 844441 | 1/1977 | Belgium | 260/141 P |
| 2635778 | 2/1977 | Fed. Rep. of Germany | 260/141 P |
| 812368 | 4/1959 | United Kingdom | 260/141 P |

OTHER PUBLICATIONS

Zollinger, H. *Azo & Diazo Chemistry: Aliphatic and Aromatic Compounds*, Interscience, 1961.

*Primary Examiner*—John F. Niebling
*Attorney, Agent, or Firm*—Cushman, Darby & Cushman

[57] ABSTRACT

A process for the diazotization of a heterocyclic or a weakly basic benzenoid amine which comprises reacting together in a continuous manner, in a reaction zone from which a product stream containing diazotized amine is continuously removed, the amine and an aqueous solution of nitrite ions in the presence of sulphuric acid, the proportions and concentrations of the amine, the aqueous solution of nitrite ions and the sulphuric acid being so arranged as to provide a working acid concentration in the reaction zone in which the diazotized amine is stable.

10 Claims, 3 Drawing Figures

PROCESS AND APPARATUS FOR THE DIAZOTIZATION OF AMINES

This invention relates to a process for the diazotisation of amines and in particular to such a process effected in a continuous manner.

It has been proposed (U.K. Pat. No. 812368) to carry out the diazotisation of amines in a continuous manner, by mixing an amine and a diazotising agent under isothermal conditions at or around 0° C. so that the diazonium compound is formed at a temperature at which it is relatively stable in an aqueous medium. It has also been proposed (U.K. Pat. No. 1082636) to effect aqueous diazotisations under adiabatic conditions without precooling of the reactants and to avoid decomposition, by reacting the diazonium compound further within a very short period of time.

Certain Benzenoid amines, such as substituted dinitroanilines and most heterocyclic amines cannot however be conveniently diazotised under aqueous conditions either because the resultant diazo compounds are unstable in aqueous media or because the rate of diazotisation is very slow in aqueous media. Such amines are therefore conventionally diazotised, in a batchwise manner, in a non-aqueous medium such as concentrated sulphuric acid. The use of such media poses operational problems associated with the introduction of the amine (usually in solid form) and the preparation of the diazotising agent. It is normal practice to employ reactants and reaction media which are essentially free from water in order to avoid the possibility of diazo decomposition and the evolution of heat.

It has now been found that it is possible to diazotise such amines in a continuous manner, using an aqueous solution of nitrite ions.

According to the present invention there is provided a process for the diazotisation of a heterocyclic or a weakly basic benzenoid amine which comprises reacting together in a continuous manner, in a reaction zone from which a product stream containing diazotised amine is continuously removed, the amine and an aqueous solution of nitrite ions in the presence of sulphuric acid, the proportions and concentrations of the amine, the aqueous solution of nitrite ions and the sulphuric acid being so arranged as to provide a working acid concentration, as hereinafter defined, in the reaction zone in which the diazotised amine is stable.

According to a first mode of operation (the one-stage mode) the process comprises mixing together in a continuous manner the amine, a sulphuric acid medium as hereinafter defined and an aqueous solution of nitrite ions and according to a second mode of operation (the two-stage mode) the process comprises mixing together in a continuous manner in the reaction zone a first stream comprising the amine either alone or in a sulphuric acid medium and a second stream comprising the product of pre-mixing together, in a pre-mix zone, in a continuous manner, a third stream comprising an aqueous solution of nitrite ions and a fourth stream comprising sulphuric acid at such rates and concentrations that the sulphuric acid concentration in the second stream is at least 65%.

It is preferred, for operational reasons, particularly in the case of the one-stage mode, that the amine is dissolved or suspended in the sulphuric acid medium before it is introduced into the reaction zone-metering and control being generally more convenient with liquid streams than with solid or paste-like media. The one-stage mode thus preferably involves two streams, the first comprising a solution or suspension of the amine in a sulphuric acid medium and the second comprising an aqueous solution of nitrite ions.

In the case of the one-stage mode all the sulphuric acid in the reaction zone is preferably added in the first stream along with the amine whereas in the two-stage mode it is preferred to divide the sulphuric acid between the first and second streams so that both are in a liquid form. It is of course possible in the latter case to introduce all the sulphuric acid in the second stream with the nitrite and to introduce the amine into the reaction zone in the form of a stream of paste or powder.

The diazotisation reaction is preferably carried out under such conditions that the streams are mixed together completely and intimately in one or more stages in a time sufficiently short to ensure a high degree of selectivity towards the reaction producing the desired product and in particular to minimise decomposition of the diazotising species before it reacts with the amine.

Although conditions of high shear in the reaction zone are preferred in order to provide rapid and efficient mixing of the reactant streams, it is not necessary that there should be any attrition or grinding of the reactants or product even where these are not completely dissolved in the reaction medium.

A convenient index for the basicity of an amine is the pKa value which is discussed in an article by Johnson et al entitled "The temperature variation of the $H_o$ acidity function in aqueous sulphuric acid solution" (JACS 91 1969 pages 6654–6662). The pKa value of a base is defined as follows:

$$pKa = pH - \log \frac{[B]}{[BH^+]} - \log \left[ \frac{f_B f_{H^+}}{f_{BH^+}} \right]$$

wherein $f_B$, $f_{H^+}$ and $f_{BH^+}$ are the activity coefficients of the base, hydrogen ion and conjugate acid respectively.

Preferred benzenoid amines for use in the present invention have pKa values in the range $-1.5$ to $-10.5$, and more preferably in the range $-2.5$ to $-7.0$.

Particularly suitable amines from the benzene series contain at least two nuclear substituents selected from nitro and cyano or at least one nuclear substituent selected from nitro and cyano and at least two further substituents selected from halogen and sulphone. Examples of such amines in the benzene series are 2,4-dinitroaniline, 2-bromo-4,6-dinitroaniline, 2-cyano-4,6-dinitroaniline, 1-amino-2,4-dinitrobenzene-6-methylsulphone, 2,6-dicyano-4-nitroaniline, 2-cyano-4-nitroaniline, 2-chloro-4-nitro-6-cyanoaniline, 2-bromo-4-nitro-6-cyanoaniline, 2-cyano-4-nitro-6-methylaniline, 2-bromo-6-chloro-4-nitroaniline and 2,6-dichloro-4-nitroaniline.

It is especially preferred that the benzenoid amines contain at least two nuclear substituents selected from nitro and cyano, and in addition, one other substituent selected from nitro, halogen or sulphone groups.

Heterocyclic amines may be derived from imidazoles, thiazoles, triazoles, pyridines, pyrazoles, benzthiazoles, thiadiazoles, thiophenes, isothiazoles, benzisothiazoles or benztriazoles.

Examples of heterocyclic amines are 2-aminothiazole, 2-amino-5-nitrothiazole, 2-amino-5-methylsulphonylthiazole, 2-amino-5-cyanothiazole, 2-amino-4-methyl-5-nitrothiazole, 2-amino-4-methylthiazole, 2-amino-4-phenylthiazole, 2-amino-4-(4'-chlorophenyl)-thiazole, 2-amino-4-(4'-nitrophenyl)thiazole, 3-aminopyridine, 3-aminoquinoline, 3-aminopyrazole, 5-amino-1-phenylpyrazole, 3-aminoindazole, 3-amino-2-methyl-5,7-dinitroindazole, 3-amino-1,2,4-triazole, 5-(methyl-, ethyl-, phenyl- or benzyl)-1,2,4-triazole, 3-amino-1-(4'-methoxyphenyl)pyrazole, 2-aminobenzthiazole, 2-amino-6-methylbenzthiazole, 2-amino-6-methoxybenzthiazole, 2-amino-6-cyanobenzthiazole, 2-amno-6-nitrobenzthiazole, 2-amino-6-carboethoxybenzthiazole, 2-amino-6-thiocyanatobenzthiazole, 2-amino-6-methylsulphonylbenzthiazole, 2-amino-1,3,4-thiadiazole, 2-amino-1,3,5-thiadiazole, 2-amino-4-phenyl- or 4-methyl-1,3,5-thiadiazole, 2-amino-5-phenyl-1,3,4-thiadiazole, 2-amino-3-nitro-5-methylsulphonylthiophene, 2-amino-3,5-dinitrothiophene, 2-amino-3-alkoxycarbonyl-5-nitrothiophene (where alkoxy=$C_1$-$C_5$), 2-amino-3-cyano-5-nitrothiophene, 5-amino-3-methyl-4-nitroisothiazole, 3-amino-5-nitro-2,1-benzisothiazole, 3-amino-7-bromo-5-nitro-2,1-benzisothiazole, 5-amino-4-nitro-1-methylimidazole, 4-amino-5-bromo-7-nitrobenzispthiazole and 4-amino-7-nitrobenztriazole.

Preferred heterocyclic amines are from the benzthiazole, triazole and thiophene classes, in particular 2-amino-6-methoxybenzthiazole, 2-amino-6-thiocyanatobenzthiazole, 3-amino-1,2,4-triazole and 2-amino-3,5-dinitrothiophene.

These amines are generally solid at room temperature and are most conveniently used in the form of a powder or a paste containing up to 60% by weight of water although it is generally preferred, where a paste is used, that it should not contain more than 20% by weight of water.

It is especially preferred that the amines do not contain substituents reactive towards concentrated sulphuric acid, other than by salt formation, or towards any other acid which may be a constituent of the concentrated acid medium.

The process is useful for the diazotisation of those weakly basic benzenoid amines, e.g. bromodinitroaniline, which form diazo compounds that are unstable in a dilute mineral acid medium at any temperature above the freezing point of the medium. Even those weakly basic benzenoid amines which can form stable diazo compounds in a dilute acid medium, i.e. <50%, must generally be maintained below 20° and preferably below 10° or even 5° C. during and after diazotisation in order to prevent excessive decomposition.

The sulphuric acid medium, i.e. a medium containing sufficient sulphuric acid to provide a "working acid concentration" in which the diazotised amine is substantially stable may contain water or other acids such as phosphoric acid and aliphatic mono- or dicarboxylic acids or mixtures of these. It is preferred that the medium comprises from 50% to 100% by weight of sulphuric acid, based on the total weight of the medium, and more preferably from 80% to 100%. Where a mixed acid medium is used it is preferred that the second acid or mixture of acids does not exceed 70% by weight of the sulphuric acid. The concentration of acid is preferably sufficient to completely dissolve the amine at molar concentrations up to 25% in order to minimise the possibility of unreacted amine passing into the product stream. It may be desirable however, in certain circumstances, to add water to the first stream immediately before mixing with the second stream, e.g. where the latter comprises a very concentrated solution of nitrite, in which case the amine may be partially precipitated from solution.

The nitrite ions in the second stream may be provided by any suitable water-soluble salt of nitrous acid, e.g. an alkali metal salt. A particularly convenient salt, in cheap and plentiful supply, is sodium nitrite which is commercially available as an aqueous solution. At least part of the sodium nitrite in the second stream may be replaced by other more soluble nitrite salts, e.g. potassium and lithium, particularly where it is desired to use more concentrated reactant streams.

In the second mode of operation, the sulphuric acid medium comprising the fourth stream, which is used to prepare the second stream, is preferably 100% sulphuric acid, i.e. containing no more than a negligible quantity of water.

In the first mode of operation, rapid mixing together of the reactants is highly desirable in order to avoid or minimise the formation of localised regions of low acid concentration, particularly in regions close to the point of entry of each of the first and second streams into the reaction zone. Such low acid concentrations can lead to the formation of nitrogen oxides and tar and also to precipitation of the amine in a form which inhibits complete diazotisation. Inadequate and slow mixing can also lead to localised hot spots in which decomposition of the reactants and product and vaporisation of the reaction medium can occur giving rise to operational difficulties.

The first and second streams may also contain other ingredients which are conventionally present in diazotisation media such as diazo stabilisers, e.g. naphthalene-1,3,6-trisulphonic acid, and surfactants, e.g. lauryl trimethylammonium salts.

The concentration of the reactant streams, i.e. of the amine in the first stream and of the diazotising agent in the second stream, may be varied within wide limits provided the concentration of acid in the reaction zone and product stream, herein referred to as the "working acid concentration", is sufficient to maintain the diazotised amine in a substantially stable condition. Throughout this specification the working acid concentration is defined in terms of the quantity of sulphuric acid and water in the reaction mixture as:

$$\frac{\text{wt. of sulphuric acid}}{\text{wt. of sulphuric acid + wt. of water}} \times 100$$

The minimum working acid concentration depends on a number of factors including the nature of the amine, the acid and the temperature. At 40° C. the rate of decomposition of diazo-dinitroaniline in 30% sulphuric acid (1% in 7 minutes) is acceptable for present purposes and even lower acid concentrations may be tolerated. At 40° C. the rate of decomposition of diazo-bromodinitroaniline in 40% sulphuric acid is much greater (1% in 17 seconds).

The stability of the diazotised amine in the reaction zone is conveniently measured in terms of the extent of decomposition before the product stream issues from the reaction zone. The working acid concentration in the reaction zone is preferably such that the diazotised amine undergoes less than 5% and more preferably less than 1% decomposition by the time it is discharged from the reaction zone in the product stream.

If the working acid concentration is too high, the precipitation of sodium bisulphate can give rise to blockages in the outlet from the reaction zone or otherwise interfere with diazotisation.

It is preferred therefore that the working acid concentration is in the range 50% to 85% with the heterocyclic and the more weakly basic benzenoid amines. Lower acid concentrations, however, can be tolerated with the less weakly basic benzenoid amines such as, for example, dinitroaniline and halomononitroanilines, or where the diazotised amine will be reacted further, e.g. coupled to form an azo compound, within such a short period of time that diazo decomposition is within the above-mentioned limits. At working acid concentrations up to 85%, amine concentration in the acid of up to 15 mole % can be tolerated without excessive precipitation of sodium bisulphate. Generally, the lower the working acid concentration, the greater the molar concentration of amine that can be tolerated without excessive precipitation of bisulphate.

If the second mode of operation is employed, it has been found that there is negligible precipitation of sodium bisulphate at working acid concentrations in the range 80–90% provided the product stream is allowed to undergo further reaction (normally coupling to form an azo dyestuff) without delay because bisulphate is only precipitated if the reaction product stream is allowed to stand.

It is preferred that the concentration of amine in the first stream is in the range 5 mole % to 20 mole % and more particularly in the range 7 mole % to 13 mole %. The concentration of nitrite is then adjusted to produce the desired working acid concentration.

It is desired to operate at a high amine concentration in the reaction zone and a high working acid concentration, precipitation of bisulphate can be further reduced by replacement of at least part of the sodium nitrite by a more soluble nitrite such as potassium or lithium nitrite which produces a more soluble bisulphate.

Where the diazotised amine is to be converted into an azo compound it is usually undesirable that the product stream should contain any free amine and therefore under ideal conditions there should be at least enough diazotising agent entering the reaction zone to diazotise all the amine. It is however preferred to have a stoichiometric excess of diazotising agent, up to 10%, in order to allow for losses. It is normally convenient to arrange for an excess in the range 2% to 5%.

The heat evolved in the reaction and pre-mix zones arising from dilution of the sulphuric acid medium when it mixes with the aqueous nitrite solution, and reaction of the diazotising agent with the amine may be considerable and in a low heat capacity system can lead to an excessive temperature rise. If necessary, this heat may be removed from the reaction and pre-mix zones by the provision of internal or external cooling means. The temperature in the reaction zone is preferably maintained in the range 20° C. to 70° C. and more preferably in the range 35° C. to 50° C. In the two-stage mode the temperature in the pre-mix zone may be permitted to rise to 100° C. or even higher.

The residence time of the reaction mixture in the reaction zone may be adjusted by altering the volume of the reaction zone or by varying the rate of flow of the reactants into and product stream out of the reaction zone.

According to further features of the present invention we provide apparatus suitable for performing the continuous diazotisation process hereinbefore defined. For the first mode of operation suitable apparatus comprises a reaction zone having an inlet line for each reactant stream and an outlet line, means for separately introducing the reactant streams into the reaction zone by way of the inlet lines at controlled rates, means for promoting rapid and efficient mixing of the reactants in the reaction zone and means for monitoring the quality of the reaction product stream in the outlet line. For the second mode, means for introducing reactant into one of the inlet lines comprises a pre-mix zone having an outlet line connected to the inlet line of the reaction zone and two inlet lines, means for separately introducing liquids into the inlet lines of the pre-mix zone at controlled rates and means for promoting rapid and efficient mixing of the liquids in the pre-mix zone.

The reaction zone may be contained within an agitated vessel into which the reactant streams are introduced preferably close together at the point of greatest agitation and from which the product stream is continuously removed.

However, to take account of the considerable heat of dilution and reaction in the one-stage mode of operation, it is convenient to perform the mixing and reaction in a recirculation loop so that the heat evolved can be more easily removed. The recirculation loop can induce the formation of stable froths in certain reaction systems. Where frothing is a problem it is desirable to include in the loop gas/liquid disengagement means, e.g. a cyclone.

The reaction zone may therefore comprise a recirculation system having a mixing zone, with inlet circulation and outlet circulation ports, into which mixing zone the inlet lines are connected, and a recirculation loop connecting the inlet and outlet circulation ports into which the outlet line is connected and through which the reaction mixture may flow during reaction.

A venturi injector or the like, in which the passage of a liquid produces a partial vacuum and turbulence, provides a suitable mixing zone. Inlet lines from storage tanks containing the reactants and leading into the throat of the Venturi at the point of maximum vacuum and turbulence provide the inlet lines for the reactant streams and ensure rapid mixing of the reactants.

A pipeline containing a pump or like means for inducing motion of liquid through the recirculation system provides a suitable recirculation loop to which may be connected an outlet pipe as the outlet means from the reaction zone.

The recirculation loop may contain a buffer vessel between the outlet circulation port of the mixing zone and the outlet means in which the reaction may pass to substantial completion.

The product stream may conveniently be removed under gravity or by means of a pump situated in the outlet pipe.

Heat evolved during mixing and reaction may be removed by a suitable heat exchanger, e.g. a cooling jacket around the reaction or buffer vessel or around part of the recirculation loop through which jacket a cooling liquid may be circulated in response to a temperature controller located in the reaction zone.

There is also preferably provided control means for adjusting the absolute or relative rates of delivery of the reactants into the reaction zone in accordance with variations in the quality of the product stream as detected by the detection means.

The detection means, which is preferably situated in the outlet means, conveniently comprises means for measuring the quantity of excess diazotising agent in the product stream and preferably provides a continuous indication of this quantity. A suitable detector for this purpose is described in Belgian Pat. No. 851,666.

Alternatively the excess diazotising agent may be determined directly by means of the redox potential between platinum and glass electrodes placed in the product stream.

If it is desired to monitor the presence of unreacted amine in the product stream, this can be effected by diluting a portion of the product stream with water and measuring the turbidity of the diluted material in a spectrophotometer in the region of 700 nanometers.

These measurements of excess diazotising agent and unreacted amine may be performed continuously or intermittently and the signals may be used to control the relative proportions and flow rates of the reactant streams by means of the control means.

Where the detecting means measures the quantity of excess diazotising agent the control means conveniently generates from the difference between the measured excess and a predetermined standard, a signal that causes the ratio of the rates of flow of reactants into the reaction zone to be altered.

In the second mode of operation (two-stage mode) the requirement for particularly efficient mixing is in the pre-mix zone where the heat of dilution of the sulphuric acid may be considerable and localised regions of low acid concentration can lead to decomposition of diazotising agent. The efficiency of mixing required in the reaction zone is less than in the first mode because the amine and agent are both stable in the partially mixed media.

The two-stage mode of operation thus has advantages in terms of improved control and operation particularly during start up and shut down but requires more control equipment than the one-stage mode of operation.

A convenient arrangement for the two-stage mode is the provision of a recirculation system for the first stage (pre-mix zone) and an agitated vessel for the second stage (reaction zone).

The invention will now be further described with reference to the accompanying drawings in which.

Figure 1:
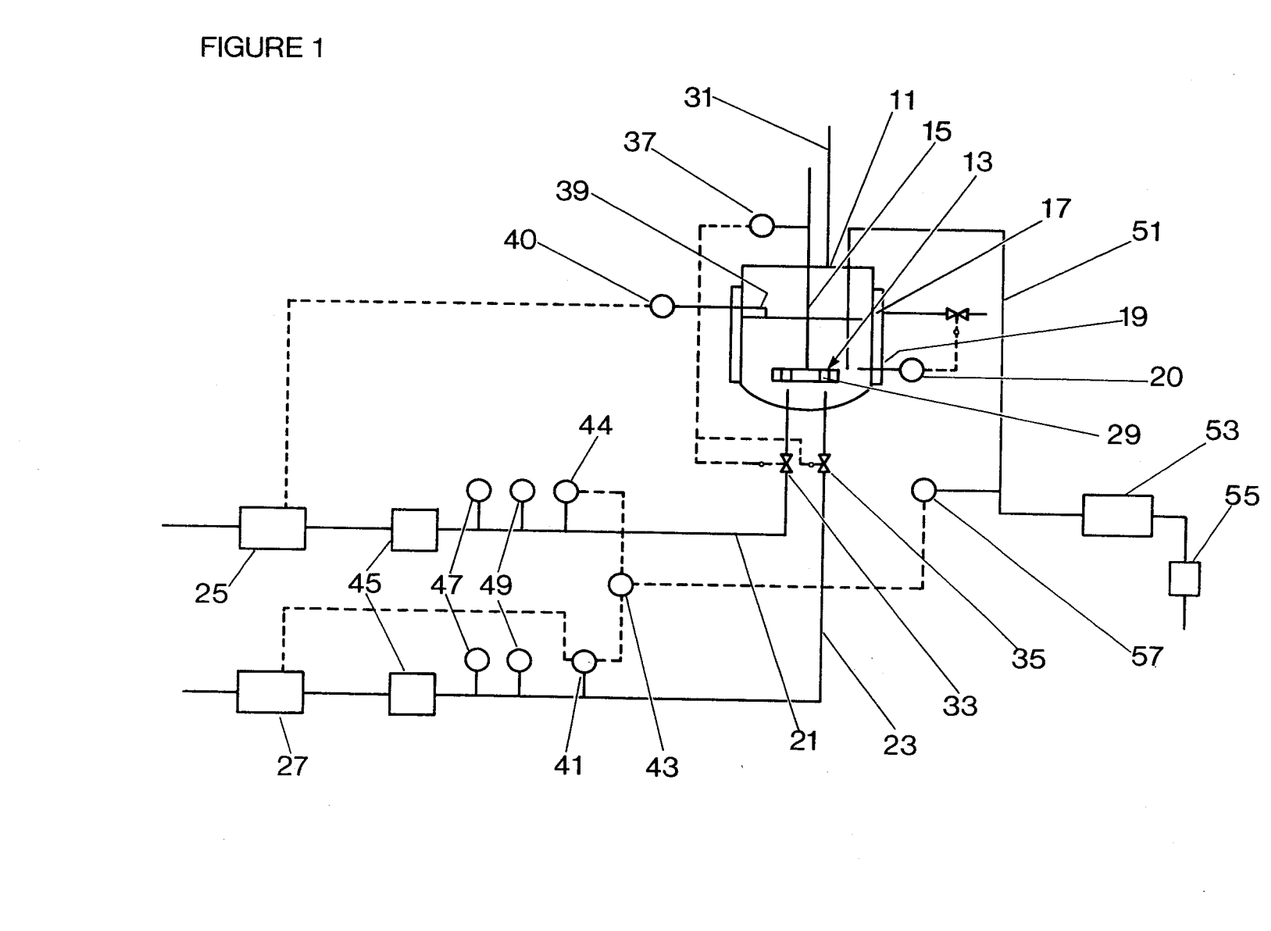
FIG. 1 is a diagrammatic representation of an apparatus for performing the process of the invention in the first mode in which the reaction zone is contained in an agitated vessel.

In FIG. 1 a closed reaction pot 11 is fitted with a high speed, high shear mixer 13 capable of maintaining the whole contents of the pot 11 in the reaction zone, in a turbulent condition. The reaction pot 11 is surrounded by a cooling jacket 17 connected to a source of cooling medium (not shown) the circulation of which is controlled by a temperature controller 20, in response to the temperature in the pot 11 measured by thermometer 19.

Two inlet lines 21, 23, from metering feed pumps 25, 27 respectively, pass through the base of the pot 11 and terminate close to the rotor 29 of the mixer 13, and a vent 31 connecting the inside of the pot 11 to atmosphere, via a scrubber (not shown), leads from the top of the pot 11. Valves 33, 35 in the inlet lines 21, 23, situated just outside the pot 11 are safety devices to prevent the addition of reagents in the event of agitator failure. They are activated by a controller 37 which closes them when the rate of rotation of the shaft 15 driving the rotor 29 of the mixer 13 falls below a predetermined value.

Feed pump 25 is connected to a level controller 40 which measures the level in the reaction pot via a level indicator 39.

Feed pump 27 is connected to a controller 41 set in inlet line 23 which is connected by a ratio controller 43 to a feed rate indicator 44 in inlet line 21. Each inlet line 21, 23 is fitted with a damper 45 immediately after the feed pump 25, 27, a pressure indicator 47 and a temperature indicator 49.

An outlet line 51, the entrance to which is situated closely above the rotor 29 of the mixer 13, passes through the top of the pot 11 and thence to a metering outlet pump 53 followed by a damper 55. A diazo monitor 57 situated in the outlet line 51 is electrically connected to the ratio controller 43.

On start up, the rotor 29 of the mixer 13 is covered with the sulphuric acid medium and set in motion. Inlet lines 21, 23 are connected to supplies of amine in the sulphuric acid medium and an aqueous nitrite solution respectively. These supplies are of predetermined, known strengths and the ratio controller 43 is set so that the feed pumps 25, 27 deliver the liquid to the pot 11 at suitable rates so that there is a slight (~5%) excess of nitrite above that needed to react with all the amine.

Rotation of the rotor 29 allows inlet valves 33, 35 to open so that the reactants are admitted into the pot 11 in the most turbulent region just below the rotor 29. When the level in the reaction pot 11 reaches the desired level the outlet metering pump 53 is started up so as to remove reaction mixture containing the diazotised amine from the reaction pot 11. The reaction mixture is maintained at the desired level by means of the control exerted by the level controller 40 over the feed pump 25. The flow rate of nitrite liquor in inlet line 23 is determined, by the ratio controller 43, by reference to the flow rate of the concentrated sulphuric acid/amine mixture in the other inlet line 21, in accordance with a predetermined setting that is dependent on the relative strengths of the amine and nitrite solutions.

The temperature in the reaction pot 11 is maintained at or below a predetermined temperature dependent on the known reactivity of the diazotised amine and its predetermined residence time in the reaction pot 11 (dependent on the feed rates of the reactants) by means of the cooling medium circulating in the jacket 17 which removes sufficient heat of dilution and reaction to maintain the temperature in the pot 11 at or below the predetermined temperature.

The residence time of the reaction mixture in the reaction zone is arranged to be sufficient for complete reaction and therefore the diazo monitor 57 merely detects excess nitrite in the product stream in the outlet line 51. If there is too large an excess or a deficiency of nitrite in the product stream the ratio controller 43 is automatically reset so as to reduce or increase the proportion of nitrite liquor entering the reaction pot 11 accordingly.

Figure 2:
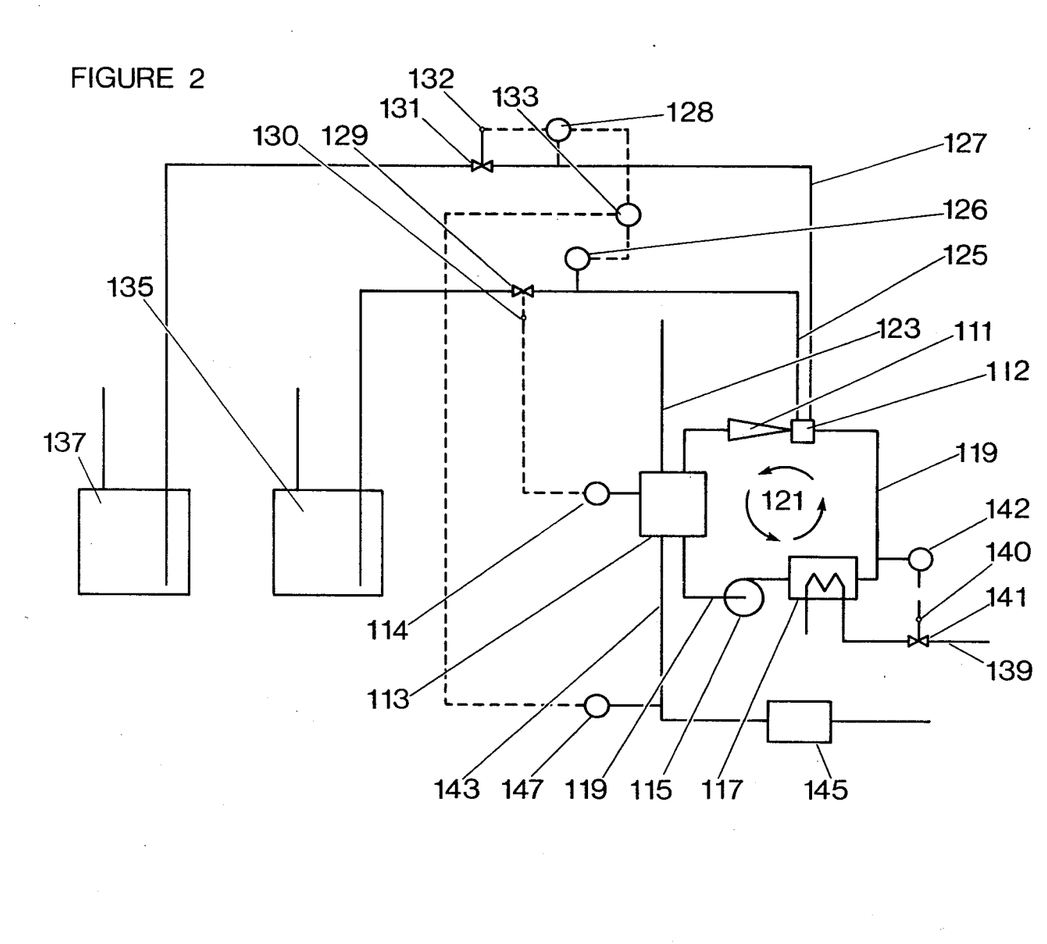
FIG. 2 is a diagrammatic representation of an apparatus for performing the process of the invention in the first mode in which the reaction zone comprises a mixing zone and a recirculation loop.

In FIG. 2 a Venturi injector 11 comprising the mixing zone is connected in series with a buffer vessel 113, a circulation pump 115 and a heat exchanger 117 by pipe line 119 items 113–119 constituting the recirculation loop 121.

The buffer vessel 113 is connected to atmosphere by a vent line 123 and a scrubber (not shown). Two inlet lines 125, 127, fitted with control valves 129, 131, lead into the throat 112 of the Venturi injector 111 from vented storage tanks 135 and 137, respectively, situated below the level of the Venturi injector 111 and recirculation loop 121. The operating mechanism 130 for control value 129 in inlet line 125 is connected to a level detector 114 in the buffer vessel 111. A flow indicator/controller 126 in line 125 is connected via a ratio controller 133 and flow indicator controller 128 in line 127 to the operating mechanism 132 of control valve 131.

A supply of cooling medium, not shown, is connected to the heat exchanger 117 by pipeline 139 containing a control valve 141 the operating mechanism 140 of which is connected to a temperature indicator/controller 142 in the pipeline 119 of the recirculation loop 121.

An outlet line 143 from the recirculation loop 119 leads from the buffer vessel 113 to a metering outlet pump 145. A diazo monitor 147, situated in the outlet line 143, is connected to the ratio controller 130.

On start up, a sulphuric acid medium containing the amine to be diazotised and nitrite liquor of predetermined proportions are placed in storage tanks 135 and 137 respectively and the recirculation loop 121 is filled, initially, with concentrated sulphuric acid. On setting the circulation pump 115 in operation, supplies of the amine/sulphuric acid medium and nitrite liquor are drawn into the throat 112 of the Venturi injector 111 where they are thoroughly mixed before passing around the recirculation loop 121 by way of the buffer vessel 113, pump 115 and heat exchanger 117. Excess heat, produced by dilution and diazotisation, above that required to maintain a predetermined temperature in the reaction zone, is removed by the heat exchanger 117 in response to the temperature indicator/controller 142.

A stream of diazotised amine is continuously removed from the loop 121 through the oulet line 143 by the metering pump 145.

The residence time of the reaction mixture in the reaction zone is arranged to be sufficient for complete reaction and therefore the diazo monitor 147 merely detects excess nitrite in the product stream in the outlet line 143. If there is too large an excess or a deficiency of nitrite in the product stream the ratio controller 133 is automatically reset so as to reduce or increase the proportion of nitrite liquor entering the Venturi injector 111.

Figure 3:
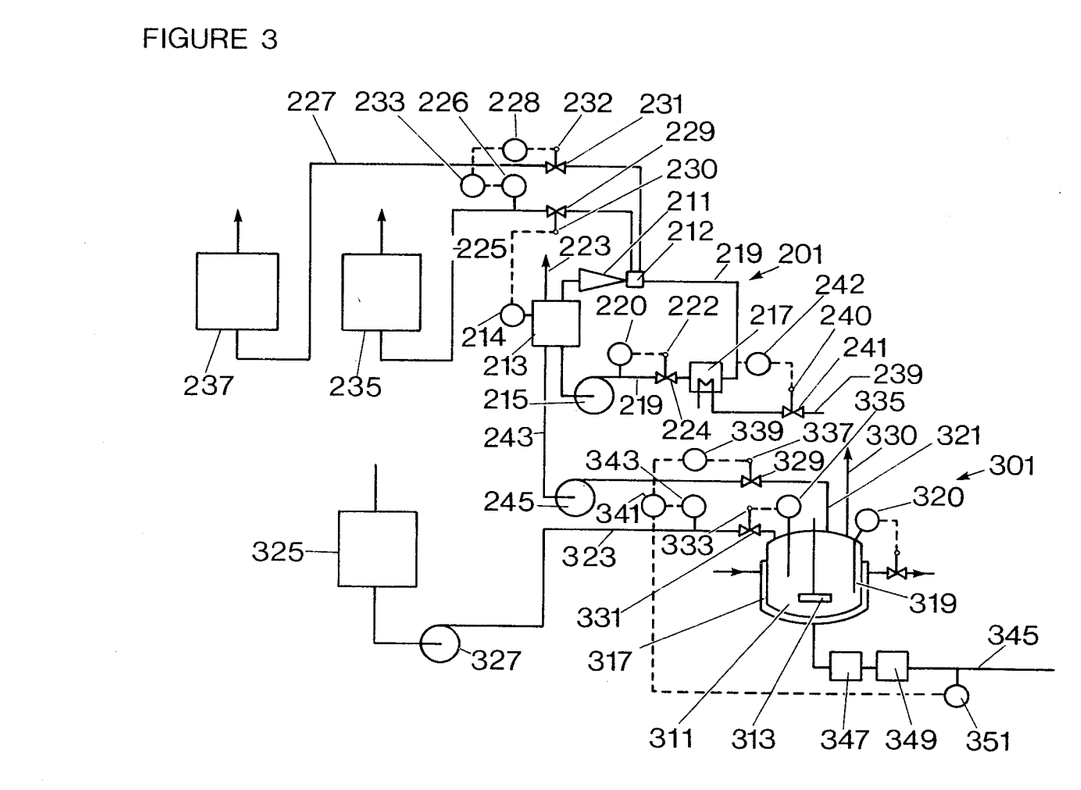
FIG. 3 is a diagrammatic representation of an apparatus for performing the process of the invention in the second mode in which the pre-mix zone comprises a recirculation system and the reaction zone is contained in an agitated vessel.

In FIG. 3 the pre-mix zone and associated equipment is generally indicated by arrow 201 while the reaction zone and related equipment is generally indicated by arrow 301.

In the pre-mix zone 201 a Venturi injector 211 comprising the mixing zone is connected in series with a buffer vessel 213, a circulation pump 215 and a heat exchanger 217 by pipe line 219, items 213–219 constituting the recirculation loop. The rate of recirculation is controlled by a flow indicator controller 220 acting on the operating mechanism 222 of a control valve 224 in pipe line 219.

The buffer vessel 213 is connected to atmosphere by a vent line 223 and a scrubber (not shown). Two inlet lines 225, 227 fitted with control valves 229, 231 lead into the throat 212 of the Venturi injector 211 from vented storage tanks 235 and 237, respectively, situated below the level of the Venturi injector 211. The operating mechanism 230 for control valve 229 in inlet line 225 is connected to a level indicator/controller 214 in the buffer vessel 213. A flow indicator/controller 226 in inlet line 225 is connected via a ratio controller 233 and flow indicator/controller 228 in inlet line 227 to the operating mechanism 232 of control valve 231.

A supply of cooling medium, not shown, is connected to the heat exchanger 217. A cooling medium outlet line 239 contains a control valve 241, the operating mechanism 240 of which, is connected to a temperature indicator/controller 242 in the pipeline 219 of the recirculation loop.

An outlet line 243 from the recirculation loop leads from the buffer vessel 213 to an outlet pump 245.

In the reaction zone 301 a closed reaction pot 311 is fitted with a propeller-type agitator 313 capable of maintaining the whole contents of the reaction pot 311 in the reaction zone, in a turbulent condition. The reaction pot 311 is surrounded by a cooling jacket 317 connected to a source of cooling medium (not shown) the circulation of which is controlled by a temperature controller 230, in response to the temperature in the pot 311 measured by thermometer 319. A first feed line 321 leads from the outlet pump 245 from the recirculation loop to the top of the reaction pot 311. A second feed line 323 leads from a vented storage tank 325 via feed pump 327 to the top of the reaction pot 311. A vent 331 connecting the inside of the pot 311 to atmosphere, via a scrubber (not shown), leads from the top of the pot 311.

Both feed lines 321, 323 carry control valves 329, 331 respectively. The operating mechanism 333 of control valve 331 is connected to a level indicator/controller 335 in reaction pot 311. The operating mechanism 337 of control valve 329 is connected via a flow indicator/controller 339 in feed line 321 and a ratio controller 341 to a flow indicator/controller 343 in feed line 323.

An outlet line 345 from the bottom of the pot 11 leads to an outlet pump 347 followed by a damper 349. A diazo monitor 351 situated in the outlet line 345 is connected to the ratio controller 341.

On start up, a sulphuric acid medium, nitrite liquor and a sulphuric acid medium containing the amine to be diazotised, each of predetermined proportions, are placed in storage tanks 235, 237 and 325 respectively and the recirculation loop is filled, initially, with concentrated sulphuric acid or a previously prepared solution of nitrosyl sulphuric acid. On setting the circulation pump 215 in operation, supplies of the sulphuric acid medium and nitrite liquor are drawn into the throat 212 of the Venturi injector 211 where they are thoroughly mixed before passing around the recirculation loop by way of the buffer vessel 213, pump 215 and heat exchanger 217. Excess heat, produced by dilution and reaction, above that required to maintain a predetermined temperature in the pre-mix zone is removed by the heat exchanger 217 in response to the temperature indicator/controller 242.

A stream of nitrosyl sulphuric acid in the sulphuric acid medium is continuously removed from the recirculation loop through the outlet line 243 by the pump 245 and fed to the reaction pot 311.

When the impellor of the agitator 313 is covered with nitrosyl sulphuric acid it is set in motion, and inlet pump 327 is set in motion. This causes the sulphuric acid medium containing amine to be fed from storage tank 325 to the reaction pot 311. The ratio controller 341 is set so that control valve 329 permits pump 245 to deliver nitrosyl sulphuric acid to the reaction pot 311 at such a rate that there is a slight (~5%) excess of nitrosyl sulphuric acid above that needed to react with all the amine.

When the level in the reaction pot 311 reaches the desired level, the outlet pump 347 is started up so as to remove reaction mixture containing the diazotised amine from the reaction pot 311. The reaction mixture is maintained at the desired level by means of the direct control exerted by the level indicator controller 355 directly over the control valve 331 and indirectly over control valve 329 via flow indicator controller 343, ratio controller 341 and flow indicator/controller 339.

The temperature in the reaction pot 311 is maintained at or below a predetermined temperature dependent on the known reactivity of the diazotised amine and its predetermined residence time in the reaction pot 311 (dependent on the feed rates of the reactants) by means of the cooling medium circulating in the cooling jacket 317 which removes sufficient heat of reaction to maintain the temperature in the pot 311 at or below the predetermined temperature.

The residence time of the reaction mixture in the reaction zone is arranged to be sufficient for complete reaction and therefore the diazo monitor 351 merely detects excess nitrosyl sulphuric acid in the product stream in the outlet line 345. If there is too large or too small an excess in the product stream the ratio controller 341 is automatically reset so as to reduce or increase the proportion of nitrosyl sulphuric acid entering the reaction pot 311 accordingly.

Many of the detailed arrangements of items shown in the drawings and described hereinbefore may be varied without departing from the concept of the invention. For example, in FIGS. 1 and 2 the feed means for each reactant may comprise a centrifugal pump and a control valve in place of the metering pump, in which case the pulsation damper may be omitted.

Where the amine is introduced into the reaction zone separately from the sulphuric acid medium then suitable powder or paste metering equipment is required.

Similarly the level indicators 39, 114, 214 and 335 shown as probes may be replaced by pressure dip pipes or differential pressure cells situated in the base of the relevant vessels.

The propeller agitator 313 shown in FIG. 3 may be replaced by a turbine or a paddle agitator capable of inducing a similar degree of motion in the reaction zone 301.

The rate of extraction of heat from the reaction pot 311 during diazotisation can be increased by the provision of a recirculation loop containing a pump and a heat exchanger. Such a loop is particularly desirable to a large installation where the volume to surface area ratio of the reaction pot 311 may be too high to permit efficient heat transfer with jacket cooling alone.

It is possible also to vary one or more of the control systems. For example, the level control system in the apparatus shown in FIG. 1 acts directly only on the amine/acid feed and thus any adjustment to the amine/acid feed rate precedes the proportional adjustment to the nitrite feed rate, which is made by the ratio controller in response to the change in the amine/acid feed rate. In an alternative arrangement to overcome the time differential between the change in the feed rates of the two streams, the flow indicator 44 in the inlet line 21 is replaced by a flow controller acting on the metering pump 25. The level controller 40 is disconnected from the metering pump 25 and connected directly to the new flow controller in inlet line 21 and indirectly, via the ratio controller, to the flow controller 41 in inlet line 23. With the new arrangement, any variation in level within the reaction pot 11 detected by level indicator 39 causes the level controller 40 to make simultaneous proportional adjustments to the flow rates in both inlet lines.

The invention is illustrated by the following Examples in which the parts and percentages are by weight unless otherwise indicated.

EXAMPLE 1

A 18.9% solution of 2,4-dinitroaniline in pure sulphuric acid is pumped at a rate of 5.32 ml/min. to a 25 ml. jacketed reaction vessel fitted with a propeller-type agitator, which is filled initially with 87% sulphuric acid. Simultaneously there is pumped to the same reactor at the rate of 2.10 ml/min. a 31.2% aqueous solution of sodium nitrite. The working acid concentration, defined as:

$$\frac{\text{parts of } H_2SO_3}{\text{parts of } H_2SO_4 + \text{parts of } H_2O} \times 100$$

is 78%, the agitator speed is 10,000 r.p.m., the residence time in the reactor is 3 minutes and the operating temperature, with cooling water flowing through the jacket, is 40°–45° C. The exit solution collected subsequent to the first 12 minutes (4 residence times) of operation was shown to contain the theoretical amount of diazonium salt based on the amine input, and the solution was shown (by absence of turbidity when diluted tenfold with water) to contain no (<½%) unreacted amine.

Table I (Examples 2–6) gives details of reactant concentration, flow rates, residence times and operating temperatures in a series of similar diazotisations using 2,4-dinitroaniline and Table II (Examples 7–12) shows the results of diazotisation using 2-bromo-4,6-dinitroaniline. In each case the derived diazonium salt solution was of satisfactory quality and prior to starting up, the reaction vessel was filled with sulphuric acid of the same concentration as the final working acid concentration.

TABLE I

| | DIAZOTISATION OF 2,4-DINITROANILINE | | | | | | |
|---|---|---|---|---|---|---|---|
| Ex. | Conc. of 2,4-dinitro aniline in 100% sulphuric acid % | Conc. of aqueous sodium nitrite % | Flow rate of amine soln. ml/min | Flow rate of nitrite ml/min | Working acid conc. % | Residence time min. | Operating temp. |
| 2 | 18.9 | 8.6 | 5.32 | 7.91 | 45 | 1.5 | 40–45° C. |
| 3 | 18.9 | 8.6 | 2.66 | 3.96 | 45 | 2.9 | 40–45° C. |

TABLE I-continued

DIAZOTISATION OF 2,4-DINITROANILINE

| Ex. | Conc. of 2,4-dinitro aniline in 100% sulphuric acid % | Conc. of aqueous sodium nitrite % | Flow rate of amine soln. ml/min | Flow rate of nitrite ml/min | Working acid conc. % | Residence time min. | Operating temp. |
|---|---|---|---|---|---|---|---|
| 4 | 18.9 | 31.2 | 2.66 | 0.952 | 78 | 5.6 | 40–45° C. |
| 5 | 18.9 | 31.2 | 5.32 | 2.10 | 78 | 2.7 | 45–50° C. |
| 6 | 18.9 | 42.0 | 2.66 | 0.654 | 85 | 5.7 | 45–50° C. |

TABLE II

DIAZOTISATION OF 2-BROMO-4,6-DINITROANILINE

| Ex. | Conc. of 2-bromo-4,6-dinitroaniline in 100% sulphuric acid % | Conc. of aqueous sodium nitrite % | Flow rate of amine soln. ml/min. | Flow rate of nitrite soln. ml/min. | Working acid conc. % | Residence time (min) | Operating temp. |
|---|---|---|---|---|---|---|---|
| 7 | 21 | 12.1 | 3.3 | 2.77 | 60 | 2.0 | 40° C. |
| 8 | 25 | 18.9 | 2.796 | 1.71 | 65 | 2.7 | 45° C. |
| 9 | 21 | 14.9 | 3.3 | 2.23 | 65 | 2.2 | 45° C. |
| 10 | 25 | 23.1 | 2.796 | 1.36 | 70 | 2.9 | 40° C. |
| 11 | 21 | 18.2 | 3.3 | 1.78 | 70 | 2.4 | 45° C. |
| 12 | 21 | 26.2 | 3.3 | 1.17 | 78 | 4.2 | 45° C. |

EXAMPLE 13

Two reactant solutions (A) and (B) are prepared. Solution (A) consists of 13.47% 2,4-dinitroaniline, 67.47% sulphuric acid and 19.06% water. Solution (B) consists of 4.83% sodium nitrite and 1.92% w/w of a condensate of ethylene oxide (20 mols) with nonyl phenol, the remainder being water.

The reaction vessel used in Example 1 is filled with a solution consisting of 30% sulphuric acid, 5% of the ethylene oxide condensate mentioned above and 65% water. After adjusting the agitator speed to approximately 5,000 r.p.m. solutions (A) and (B) are pumped simultaneously to the reactor at rates of 10.7 pts/min. and 11.4 pts/min. respectively. No cooling is applied to the jacket. When approximately three residence times have elapsed from the start of the reactant pumping the reactor has achieved steady state conditions. A slight excess of nitrous acid can be detected in the product stream which leaves the reactor at 52° C. There is no unreacted amine in the product stream and the yield of diazonium salt as measured by coupling with phenylmethylpyrazolone is quantitative.

In order to check the quality of the diazonium salt solution thus produced the output from the reactor is directed for a period of 25.4 minutes (equivalent to 0.2 g. mol. of 2,4-dinitroaniline fed to the reactor) on to a stirred solution of 3-acetylamino-N,N-bis-(2-methoxycarbonylethyl)aniline (0.2 g. mol.) in ice/water, which is maintained at 0°–5° C. during the addition. When coupling is complete the slurry is neutralised to pH 4 using sodium hydroxide liquor and the dyestuff is isolated conventionally in a yield equal to 95% of theory. When formulated as a disperse dyestuff the physical and dyeing properties of the dispersion are equal to those of the same dyestuff prepared by conventional batch diazotisation.

EXAMPLE 14

A 30% aqueous solution of sodium nitrite and 100% sulphuric acid are drawn into the recirculation loop of the pre-mix zone 201 shown in FIG. 3 at the rate of 10.7 and 30.7 pts/min. respectively. The recirculation rate in the recirculation loop is 3300 pts/min. and the mean residence time is 23.6 minutes. The temperature is maintained at 40°–45° C. by passing cooling water through the heat exchanger 217.

The product, a 13.8% solution of nitrosyl sulphuric acid is transferred at a rate of 41.4 pts/min. via outlet line 243, pump 245 and feed line 321 into the reaction pot 311 to which is also fed a solution of 2-bromo-4,6-dinitroaniline in 100% sulphuric acid (mol. ratio 1:4) at a rate of 27.4 pts/min. via feed line 323. The residence time in the reaction pot is 3.7 minutes. The product emerging from the reaction pot via outlet line 345 is a practically clear solution containing a trace of suspended solids. On pouring this solution into ice cold water, a clear solution is obtained indicating that diazotisation is complete.

EXAMPLE 15

To the stirred reaction vessel used in Example 1 are pumped simultaneously, through separate inlets, (A) a solution consisting of 14% 2-cyano-4-nitroaniline and 86% sulphuric acid at a rate of 1.43 parts/minute, (B) a solution consisting of 3.06% sodium nitrite, 1.06% of a condensate of nonly phenol with 20 moles of ethylene oxide and 95.88 parts of water at a rate of 3.68 parts/minutes and (C) a solution consisting of 30% sulphuric acid, 10% of the above-mentioned surfactant and 60% water at a rate of 4.8 parts per minute. Addition of the product stream issuing from the reactor to an ice-cold solution of N,N-bis-acetoxyethyl-m-toluidine causes the formation of a rubine disperse dye.

EXAMPLE 16

In this Example 2-amino-6-methoxybenzthiazole is diazotised by the two-stage mode of operation.

A 6.23% solution of nitrosyl sulphuric acid is prepared by the process described in the first part of Example 14, the product being continuously diluted from 13.8% to 6.23% by mixing with 70% sulphuric acid.

To the second stage (diazotisation) reactor, which comprises an open-top vessel of volume 40 cm$^3$ fitted with an Ultra-Turrax agitator having an external shaft diameter of 18 mm, are fed at a constant rate and at ambient temperature the above-mentioned 6.23% solution of nitrosyl sulphuric acid, at a rate of 22 g/min., and powdered 2-amino-6-methoxybenzthiazole at a rate of 1.8 g/min. Product is pumped from the reactor at such a rate as to maintain a constant level therein corresponding to a residence time of 2 minutes.

In order to demonstrate the satisfactory quality of the diazonium salt so produced the product emerging from the above reactor was coupled batchwise on to N-ethyl-N-(2-hydroxyethyl-)aniline as follows:

A solution was prepared consisting of N-ethyl-N-(2-hydroxyethyl-)aniline (16.5 g.), acetic acid (20.0 g.), sulphuric acid (10.0 g.), sulphamic acid (2.0 g.) and water (1000 ml.). Ice was added to reduce the temperature to <2° C. The product emerging from the diazotisation reactor over a period of 10 minutes was added with good stirring to the above solution, ice being added as necessary to maintain the temperature <2° C. The resulting suspension was neutralized to pH 4 and the dyestuff isolated by filtration. The expected dyestuff was obtained in a yield of 53% of theory and was shown by thin layer chromatography to be identical to material produced via a conventional batch diazotisation procedure.

We claim:

1. A process for the diazotisation of a heterocyclic or a weakly basic benzenoid amine which comprises reacting together in a continuous manner, in a reaction zone from which a product stream containing diazotised amine is continuously removed, the amine and an aqueous solution of nitrite ions in the presence of sulphuric acid, the proportions and concentrations of the amine, the aqueous solution of nitrite ions and the sulphuric acid beig so arranged as to provide a working acid concentration in the reaction zone in which the diazotised amine is stable.

2. A process according to claim 1 which comprises mixing together in a continuous manner the amine, a sulphuric acid medium and an aqueous solution of nitrite ions.

3. A process according to claim 2 wherein a first stream comprising the amine dissolved or suspended in the sulphuric acid medium is mixed with a second stream comprising an aqueous solution of nitrite ions.

4. A process according to claim 3 wherein the concentration of amine in the sulphuric acid medium is in the range 5 mole % to 20 mole %.

5. A process according to claim 1 which comprises mixing together in a continuous manner in the reaction zone a first stream comprising the amine either alone or in a sulphuric acid medium and a second stream comprising the product of pre-mixing together, in a pre-mix zone, in a continuous manner, a third stream comprising an aqueous solution of nitrite ions and a fourth stream comprising sulphuric acid at such rates and concentrations that the sulphuric acid concentration in the second stream is at least 65%.

6. A process according to any one of claims 1 to 5 wherein the amine is benzenoid and has a pKa value in the range −1.5 to −10.5.

7. A process according to claim 6 wherein the amine contains at least two nuclear substituents selected from nitro and cyano or at least one nuclear substituent selected from nitro and cyano and at least two further substituents selected from halogen and sulphone.

8. A process according to claim 2 wherein the sulphuric acid medium comprises from 50% to 100%, by weight, sulphuric acid.

9. A process according to claim 1 wherein the working acid concentration is such that the diazotised amine undergoes less than 5% decomposition during its residence in the reaction zone.

10. A process according to claim 1 wherein the working acid concentration in the reaction zone is in the range 50% to 85% by weight.

* * * * *